United States Patent [19]
Southern et al.

[11] Patent Number: 6,080,585
[45] Date of Patent: *Jun. 27, 2000

[54] METHODS FOR DISCOVERING LIGANDS

[75] Inventors: Edwin Mellor Southern, Kidlington; Kalim Ullah Mir, Bradford; Stephen Charles Case-Green, Oxford, all of United Kingdom

[73] Assignee: Oxford Gene Technology Limited, Oxford, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/676,140
[22] PCT Filed: Feb. 1, 1995
[86] PCT No.: PCT/GB95/00209
§ 371 Date: Oct. 2, 1996
§ 102(e) Date: Oct. 2, 1996
[87] PCT Pub. No.: WO95/21265
PCT Pub. Date: Aug. 10, 1995

[30] Foreign Application Priority Data

Feb. 1, 1994 [GB] United Kingdom ................... 9401833

[51] Int. Cl.⁷ ............................ G01N 33/00; C12Q 1/68; C12P 19/34; C07H 21/04
[52] U.S. Cl. ................................ 436/94; 435/6; 435/91.1; 536/23.1; 536/24.3
[58] Field of Search ........................... 435/4, 6, 7.1, 183; 436/501, 94; 536/24.3, 23.1, 24.5; 935/77, 78

[56] References Cited

U.S. PATENT DOCUMENTS

| | | | |
|---|---|---|---|
| 4,563,417 | 1/1986 | Albarella et al. | 435/6 |
| 4,921,788 | 5/1990 | Deutsch | 435/6 |
| 5,270,163 | 12/1993 | Gold et al. | 435/6 |
| 5,429,807 | 7/1995 | Matson et al. | 422/131 |
| 5,474,796 | 12/1995 | Brennan | 427/2.13 |
| 5,475,096 | 12/1995 | Gold et al. | 536/23.1 |
| 5,510,270 | 4/1996 | Fodor et al. | 436/518 |
| 5,635,385 | 6/1997 | Leopold et al. | 435/325 |
| 5,700,637 | 12/1997 | Southern | 435/6 |

FOREIGN PATENT DOCUMENTS

| | | |
|---|---|---|
| WO93/09668 | 5/1993 | WIPO . |
| WO93/22678 | 11/1993 | WIPO . |
| WO93/22680 | 11/1993 | WIPO . |
| WO94/05394 | 3/1994 | WIPO . |

OTHER PUBLICATIONS

Southern et al., "Analyzing and Comparing Nucleic Acid Sequences by Hybridization to Arrays of Oligonucleotides: Evaluation Using Experimental Models" Genomics 13:1008–1017, 1992.

*Primary Examiner*—Bradley L. Sisson
*Attorney, Agent, or Firm*—Wenderoth, Lind & Ponack, L.L.P.

[57] ABSTRACT

A method of identifying one or a combination of ligands, e.g. oligonucleotides or analogues, that interact specifically with a target, e.g. a DNA or an RNA molecule having a secondary or tertiary structure. One ligand may be pre-reacted to open up the target for interaction with other ligands forming an array on a solid surface.

13 Claims, 15 Drawing Sheets

Fig. 1.

An array of all tetranucleotides

Hybridisation of tRNA$^{phe}$
to an array of the type $N_3X_2N_3$ tRNA with cooperative antisense interactions

HIV RRE ELEMENT

agccagatctgagcctgggagctctggc

METHODS FOR DISCOVERING LIGANDS

BACKGROUND OF THE INVENTION

1. Field of the Invention

Interactions between molecules form the basis of most biological processes; understanding these interactions is important for the development of applications in basic research and medicine. For example, many drugs act by binding to specific receptor molecules. The task of finding ligands that bind to a given target with high specificity and affinity is often difficult and though the introduction of combinatorial chemistries will make this task easier, it is likely that single ligands for a single biological target may not be effective enough for some purposes; for example, where the aim is to block completely a specific process.

The present invention describes novel ways of discovering combinations of ligands which act together to produce more specific and stronger interactions than can be achieved by a single ligand.

2. Description of Related Art

There are two distinct ways in which ligands could act cooperatively:

Many biologically important macromolecules or macromolecular assemblages, such as proteins and RNA, are held in their active conformation by intramolecular interactions based on weak forces. Binding one ligand to the molecule partially opens its structure, and, as we will show, may expose it to other ligands which cannot bind in the absence of the first ligand. These additional ligands will reinforce the attenuation of the target molecule.

Many biological processes occur as a result of a series of reactions, each one dependent on a different macromolecule; for example, most of the pathways that produce metabolites involve a series of steps catalysed by a number of enzymes. Each enzyme could be targeted by a different ligand to produce a greater effect on the flux through the pathway than would be produced by any one. A further benefit of using combinations of agents is that it would prevent the development of resistance to the therapy: it is a major problem in the use of antibiotics and anticancer agents that, after a time, resistance develops as a result of mutation. If the agents comprised a mixture that targeted different molecules in the cell, multiple mutations would be required to produce resistance. Clearly, the chance of a cell undergoing two random mutations that coincide two produce resistance to two agents is much less likely than the single mutation required to overcome the effects of a single agent.

THE INVENTION

The invention provides a method of comparing ligands which method comprises: providing a target which is a polymeric molecule having an intramolecular structure, and a plurality of different ligands in the form of an array on a solid surface; applying the target in solution to the array of ligands; and observing quantitative differences between interactions of the target with different ligands of the array; provided that, when the ligands are not oligonucleotides or oligonucleotide analogues, then the target is a nucleic acid.

The invention also provides a method of determining combinations of ligands specific for a target, which method comprises the steps of:

a) binding at least one ligand to the target, to form a target complex, b) applying the target complex to other ligands which form an array on a solid surface, under conditions which allow interaction between the other ligands and the target complex, and c) identifying at least one other ligand which interacts with the target complex.

BRIEF DESCRIPTION OF THE FIGURES

FIG. 1 is an illustration of an array of all tetranucleotides.

DETAILED DESCRIPTION OF THE PREFERRED EMBODIMENT(S)

Figure 2A:
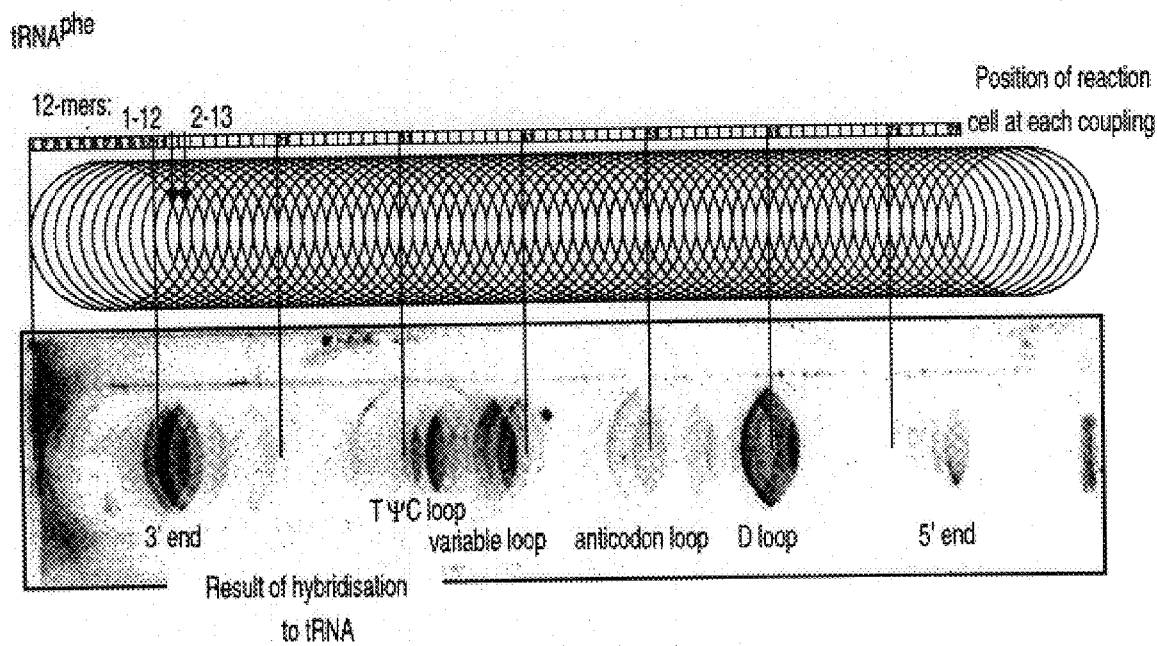
FIGS. 2(a) and (b) depict scanning arrays of oligonucleotide precursors applied in a circular patch.

A target is a polymeric molecule having an intramolecular structure such as a nucleic acid (DNA or RNA) or a protein or carbohydrate, or a macromolecular assembly such as a membrane. Targets which are compound molecules such as glycosylated nucleic acids are envisaged. A ligand is a molecule capable of interaction with a target which interaction can form the basis of therapeutic intervention or a biological test. The nature of the interaction is not material to the invention, and may for example be hybridisation or an immune reaction or any other specific binding reaction including covalent binding. Examples of ligands are oligonucleotides, peptides, steroids and glycosides.

The invention is particularly concerned with targets that have secondary or tertiary structure. So far as nucleic acids are concerned, RNA targets often have more structure than DNA targets, and are accordingly preferred. Interaction between a target and ligands on a solid surface is preferably effected under conditions such that the secondary or tertiary structure of the target is retained. For hybridisations between polynucleotide sequences for example, such conditions are well known and are different from the more stringent conditions generally used for standard DNA hybridisation reactions.

Antisense oligonucleotides

Antisense oligonucleotides and RNAs have potential as therapeutic agents, and offer one of very few methods for rational design of therapies for a range of infectious agents including viruses, bacteria and parasites, and for the treatment of cancer. For basic biological studies, they offer a way of finding a link between a gene and its functions. The need for this becomes more important as genome analysis produces increasing amounts of sequence data from uncharacterised genes. In some systems, most notably the yeasts, genes can be targeted by homologous recombination of cloned sequences, but other systems, particularly higher eukaryotes, are less amenable and antisense methods could provide simpler and more general means of attenuating or removing gene activity.

The main attraction of antisense agents is their potential to target any gene of known sequence; molecules can be designed to interact specifically with DNA and/or RNA molecules and interfere with expression by blocking replication, transcription or translation or by causing degradation by nucleases, or in the case of ribozymes, by directly degrading the target RNA. The feasibility of using antisense oligonucleotides as therapeutic agents has been demonstrated in the case of duck hepatitis virus where phosphorothioate analogues were shown to cause complete inhibition of infection in cultured cells and in animals [Offensperger et al., 1993]. Other experimental tests have met with mixed success [see James; 1991, for reent review], and it is clear that if the full potential of the method is to be realised, a number of problems must be solved. Stability of the oligonucleotides to degradation can be overcome by using analogues, but little is known about the mechanisms by which oligonucleotides enter cells. Several studies have shown that some positions in a target sequence are much more susceptible than others and that the major factor influencing the inhibitory effect of an oligonucleotide is the strength of the interaction with the target. Our own work and that of others has shown that the main factor influencing the strength of interaction between RNA molecules and oligonucleotides is intramolecular structure in the target sequence.

There is no reliable way of predicting the interaction between an oligonucleotide and its target, and so the design of antisense reagents is largely based on informed guesswork. The methods described below provide a rational strategy for choosing antisense reagents based on novel experimental systems which can be used to measure the strength of interaction between a target sequence and all potential antisense reagents. The methods can be used to find those oligonucleotides or analogues which bind most effectively to a target sequence. The methods can be extended to find combinations of oligonucleotides which act cooperatively to open up the structure of the target, enhancing each other's binding. Antisense reagents to different RNAs, providing cooperative attenuation of the activity in a biological process involving more than one gene product, can readily be found by analysing the RNAs in the way described. The same methods can be used to find antisense targets in cells where nothing is known about specific gene expression. These targets may be single RNAs or mixtures.

The methods to be described provide an entirely new approach to antisense design. It can readily be seen that the methods described for systems based on nucleic acids could be adapted to any other system for which suitable chemical procedures already exist, or could be developed.

Arrays of ligands

To test interactions between a target molecule and large number of ligands, it is convenient to make the ligands on the surface of a solid substrate, where they can all be reacted and analysed simultaneously. Large arrays of synthetic oligonucleotides can be made on the surface of a glass plate or plastic sheet [Maskos and Southern, 1992a, 1992b; Southern, Maskos and Elder, 1992; Matson, Rampal and Coassim, 1994]. Hybridisation of labelled target sequence measures the strength of interaction with each oligonucleotide in the array. For the applications described here we use three main types of array:

1. Oligonucleotides are created as lines on the surface of the substrate; target interactions with the oligonucleotides are analysed by applying a solution of the target in lines orthogonal to the oligonucleotides under conditions which will permit hybridisation to take place. In this way multiple oligonucleotides can be analysed in parallel against several targets, or the same target under different hybridisation conditions [Maskos and Southern, 1992a, 1993a]

Figure 1:
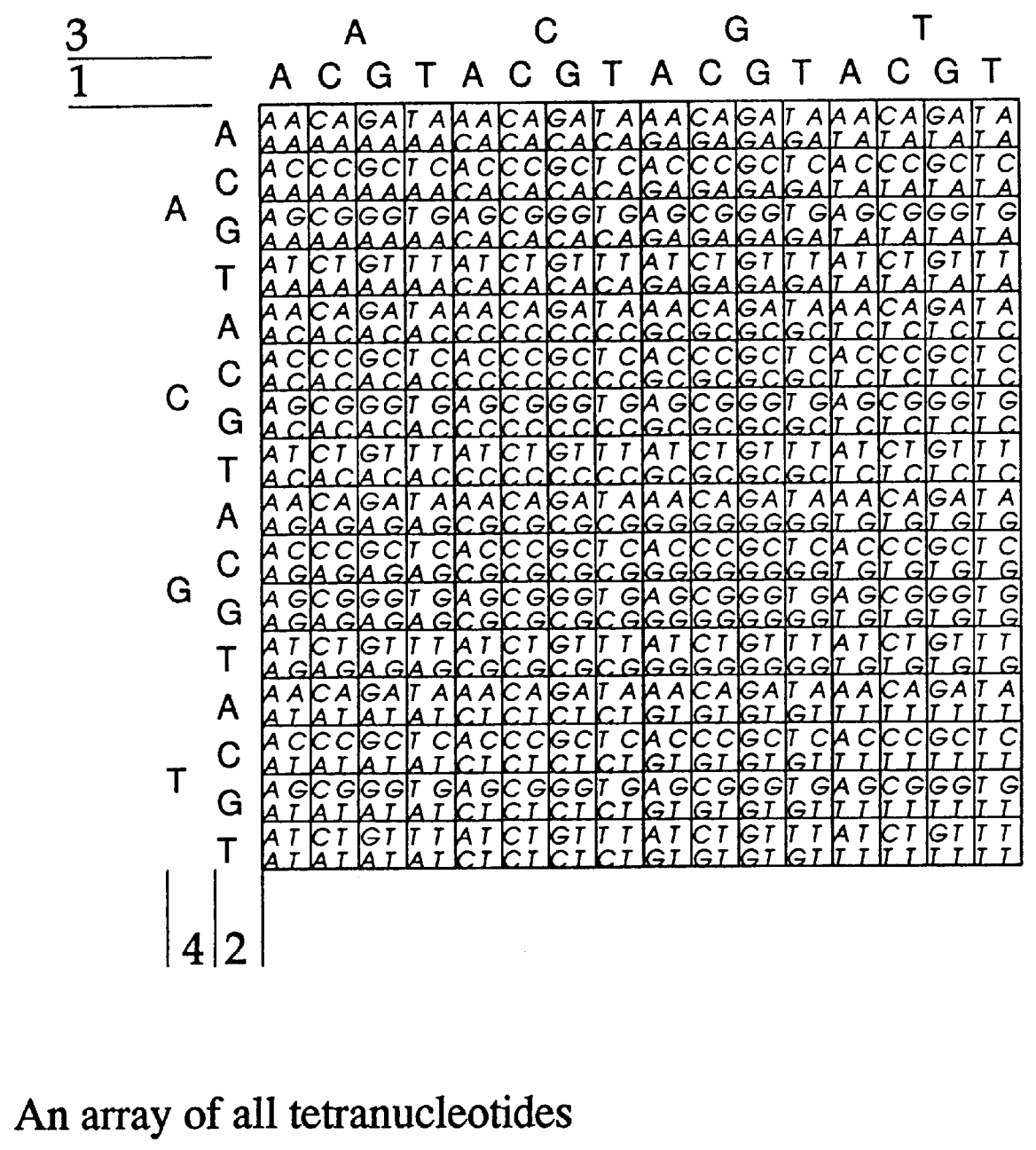

2. Complete sets of oligonucleotides of a chosen short length are made by efficient combinatorial methods; for example, we are able to make all 4096 hexanucleotides on an array 6.5cm×6.5cm in a six step synthesis (FIG. 1) [Southern, Maskos and Elder, 1992]. Such arrays can be used to explore interactions of oligonucleotides with the target even when no prior sequence information is available. These arrays are used in two strategies described below: one describes the identification of oligonucleotides which bind to a known nucleic acid sequence with the object of finding those regions which are available for binding, and thus not bound up by intramolecular structure; the second strategy describes the identification of potential antisense targets in a population of mRNAs in a differentiated cell when no prior sequence information is available.

3. "Scanning arrays" are made by stepwise synthesis in a reaction chamber which is progressively displaced along the surface of the substrate, introducing the precursor to the bases in the target sequence at each step. A single procedure, equivalent to synthesising one long oligonucleotide, creates a set of oligonucleotides which represent the entire sequence of the target molecule; each oligonucleotide in the set represents a "window" on the sequence. The width of this window can be predefined—typically we use a window of 10–15 bases and it is an important feature of the method for making scanning arrays that oligonucleotides of all lengths from a single base to this chosen length are made in the same process (FIG. 2).

Effects of intramolecular structure on ligand binding

Many biological macromolecules, including proteins, RNA and DNA, are folded into relatively stable structures which are important for biological activity. The structure is dependent on the primary sequence of the macromolecule, and also on weak intramolecular interactions based on hydrogen bonding, hydrophobic interactions etc. The macromolecule may also be bound up with other molecules, as for example would be a mRNA with proteins in a cell. A consequence of molecular folding is that some residues in the molecule are more accessible to interaction with ligands than others; this is of great importance in the design of drugs, which must bind to their target molecule.

We illustrate the problem of finding ligands that can bind to a folded macromolecule with reference to tRNA$^{phe}$, a molecule with well characterised structure. First, labelled RNA was hybridised to a general array of the type $N_3X_2N_3$, under non-stringent conditions which would retain the folded structure of the RNA molecule. The pattern revealed that only a few regions of the 76 base sequence were open to hybridisation (FIG. 3 and the legend which describes the construction of the array).

Figure 2B:
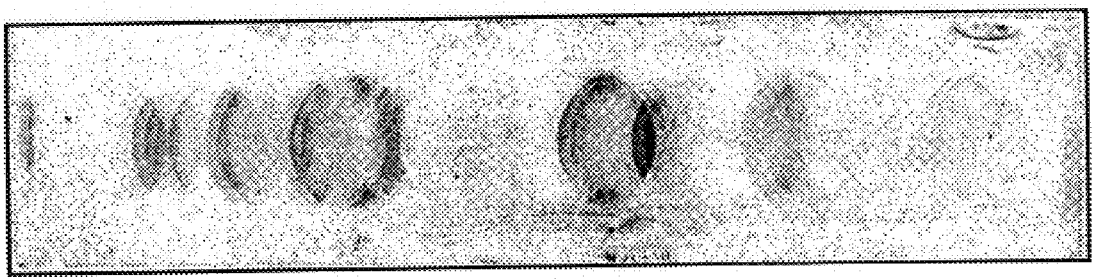

A scanning array was then made in which the oligonucleotides comprised twelve sets, each of 76 oligonucleotides, ranging in length from mononucleotides to 12 mers, representing the complement of the sequence of yeast tRNA$^{phe}$. Such an array can be made in one 76 step synthesis (FIG. 2a). Hybridisation of labelled tRNA to this array gives a pattern which shows how the oligonucleotides interact with all regions of the native molecule (FIG. 2a). In this example, the target presented to the general array of the type $N_3X_2N_3$ (where N is any one of the four bases and X is a mixture of all four bases) was so short (76 bases) that it was possible to make a scanning array of oligonucleotides representing the entire sequence. With a longer target, the general array would be used to identify regions of interest which would then be explored more thoroughly by means of one or more scanning arrays.

This experiment illustrates how secondary and tertiary structure play the dominant part in determining interactions. However, it is important to note that it is not possible to predict the strength of interaction, even in this case where the structure is known in great detail from X-ray diffraction studies. Some interactions of complementary oligonucleotides with the tRNA molecule agree with expectation: the strongest interactions are with the D-loop, the variable loop, and the 3'-end, all of which have unpaired bases. On the other hand, the 5'-end of the molecule and the anticodon loop, which we expected to be available for pairing, show only weak interactions. Similar studies, with parts of HIV RNA (FIG. 2b) and with transcripts from exons of the CFTR gene showed that some interactions occur in regions where computer predictions indicate the presence of unpaired bases, but others do not, and most importantly for the design of antisense reagents, some apparently open regions do not interact with complementary oligonucleotides.

The strength of interaction, measured from the intensity of hybridisation, is very variable, with more than 10000-fold ratio of the strongest to the weakest. It is a major benefit of the technique that the strength of interaction can be seen immediately from examination of the hybridisation pattern. It is also possible to distinguish effects due to structure in the target from those which are due to structure in the oligonucleotides; this is important information for making choices of oligonucleotides for antisense applications. A striking feature of all analyses we have done with natural RNAs is that only a very small number of sites interact strongly with complementary oligonucleotides, and we often find that the strength of interaction changes abruptly as a result of adding or subtracting a single base (e.g. the HIV-TAR analysis shown in FIG. 2b). These patterns of hybridisation, which are crucially important for the design of antisense reagents, could only be predicted from theory if a great deal were known about the structure of the RNA molecule, and if the algorithms used to calculate the relative strength of interaction of different oligonucleotides were greatly improved over those available at present. There is no other experimental system that could give the information provided by the arrays.

Identification of ligands which act cooperatively on a folded target

Figure 4:
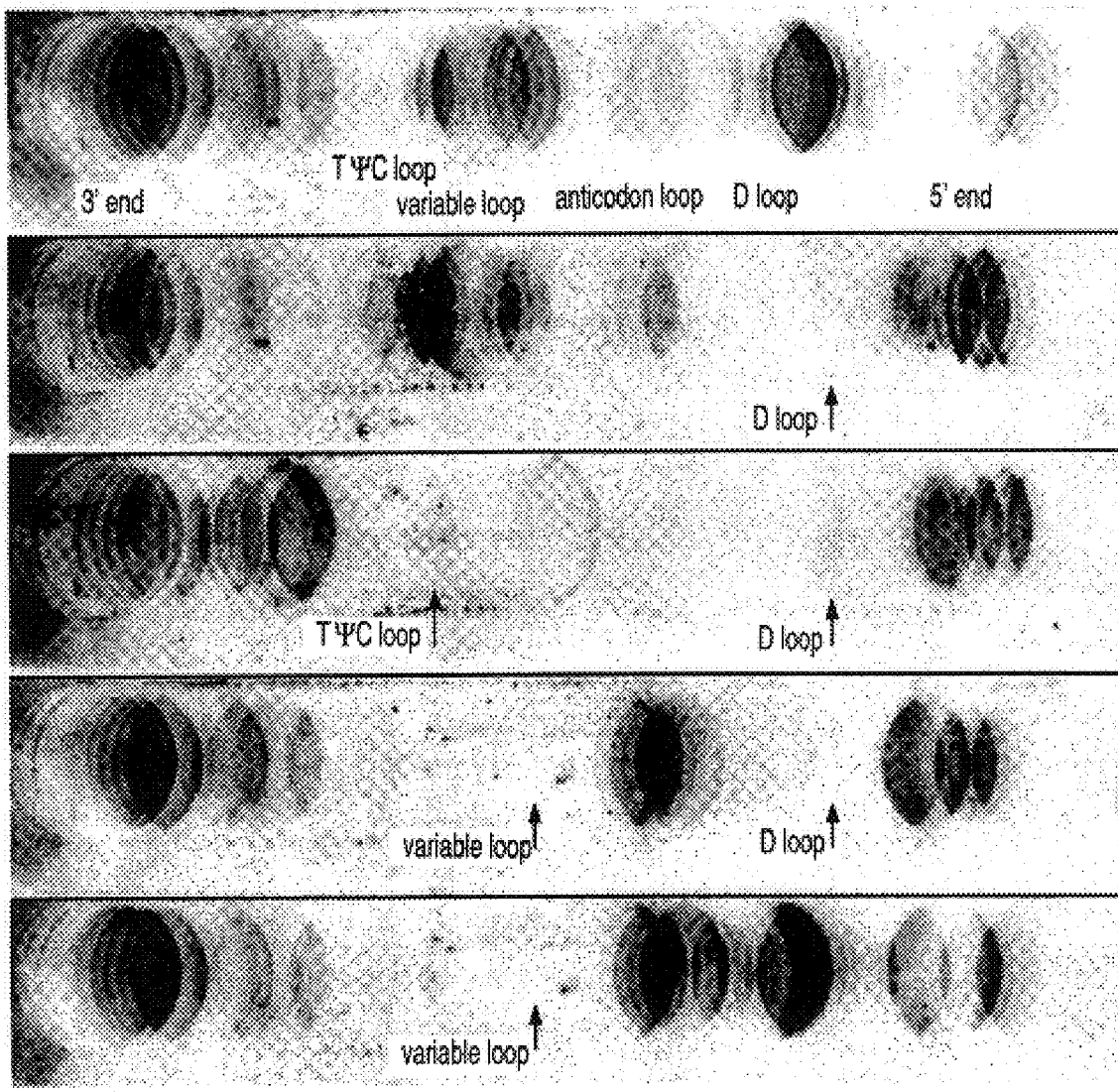
FIG. 4 shows the effect of including non-radioactive oligonucleotides with the tRNA target in a hybridisation solution.
Figure 5:
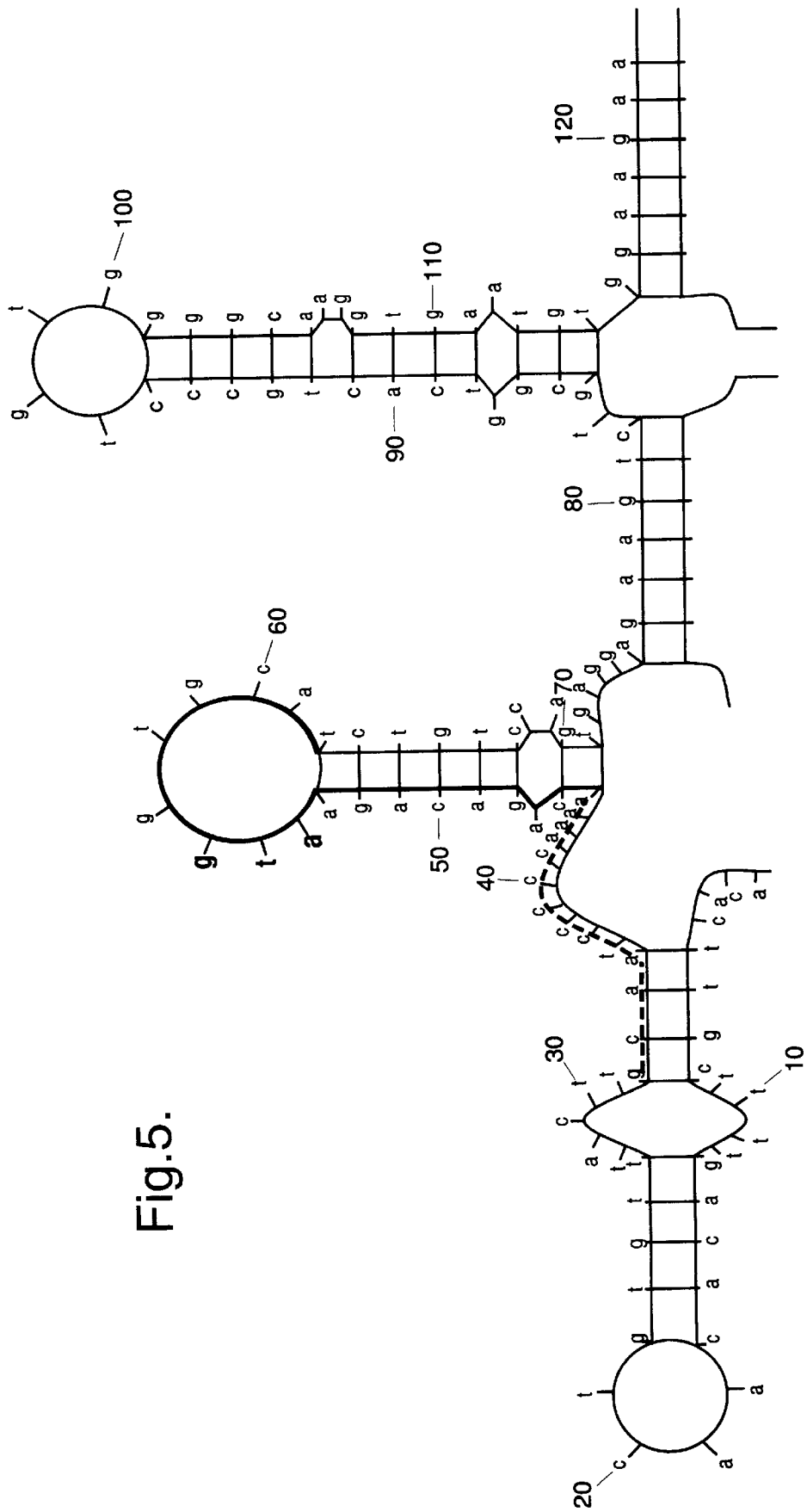
FIG. 5 shows the sites of hybridisation of cooperative antisense oligonucleotides to the structure of rabbit β-globin mRNA.
Figure 6:
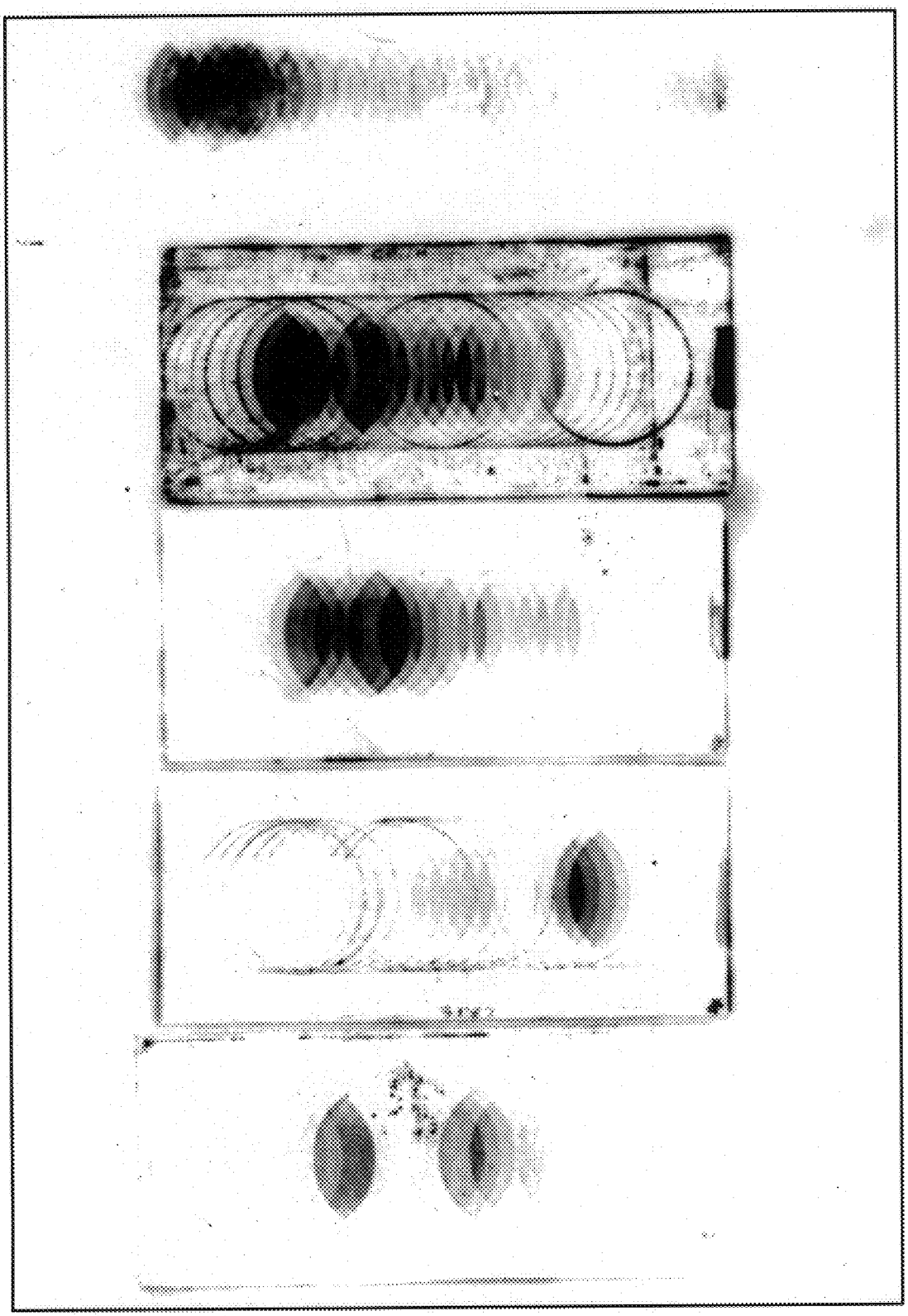
FIG. 6 shows four arrays of complements to a region of human CFTR gene.

Studies of a number of mRNAs using the method described above show that most bases are unavailable for pairing with oligonucleotides. However, when a first oligonucleotide does bind it is likely to break internal structures, releasing other bases from intramolecular pairing, and making them available for pairing with antisense oligonucleotides which would not bind in the absence of the "pioneer". This prediction was borne out in experiments with tRNA. Oligonucleotides which bound strongly to the D-loop and the variable loop of the native RNA were identified from their position on the scanning array. When an excess of oligonucleotides of these sequences (solution ligands) were added to the tRNA probe, hybridisation to the scanning array showed dramatic increase in binding to regions which bound weakly or not at all in the absence of added oligonucleotide (FIG. 4). The process can be repeated—oligonucleotides that bind in the presence of the pioneer are included with it in the hybridisation—yet other regions are opened up and seen on the scanning array. Continuation of this procedure can bring most or all of the target into duplex with oligonucleotides. Clearly the combined oligonucleotides identified by this rational stepwise analysis will produce a stronger "antisense" activity than can be achieved by any single oligonucleotide. A further benefit of this as an approach to antisense design is that multiple short oligonucleotides are likely to be more specific to the target, to be taken up more effectively by cells, to be effective at lower concentrations [Morgan et al., 1993], and may be less prone to degradation than longer ones. In several of our analyses we have found that interactions involving very short oligonucleotides—tetra-, tri- and even dinucleotides- are stronger than any between long, fully complementary oligonucleotides; it is unlikely that these interactions are due to conventional Watson-Crick pairing and thus represent unexpected interactions which are revealed by the method proposed here, and which are relevant to the design of antisense reagents.

Antisense reagents are not normally composed of oligonucleotides made from natural nucleotides, but from analogues. The important features are that:
1. They should bind specifically to a target sequence.
2. They should be able to enter the target cell.
3. They should be resistant to degradation in the cell.
4. They should induce either breakdown of the target nucleic acid or block its function.

These criteria are matched better by some modified oligonucleotides and/or analogues than by natural oligonucleotides. The chemistry that is used to synthesise analogues is readily adaptable to making arrays, and so the strategy described here can be adapted to any analogue. Furthermore, there are numerous potentially desirable modifications, for example the addition of moieties which would favour penetration of the cell or enhance binding to the target molecule whose effects on binding are not readily predictable. The array methods would allow these measurements to be carried out in a simple and straightforward way, provided that a synthetic route could be found to make the necessary structure on the array; this is the case for most of the useful modifications known at the present time.

Other ligand/target interactions

Clearly, the principles illustrated by reference to antisense oligonucleotides could be used to discover combinations of ligands of other types. The essentials are:

It must be possible to make an array of one of the potential ligand types in which the identities of the ligands occupying different cells of the array are known.

It must be possible to detect the interaction of the target molecule with the ligands in the array.

It should be noted, however, that the target, the solution ligand and the ligands on the array need not necessarily be of the same molecular type. For example: arrays of oligonucleotides could be used in conjunction with intercalating agents in solution, and vice versa to study effects of different intercalating agents on oligonucleotide binding; different types of drugs could be used in solution and on the array to study interactions with a target protein.

Ligand libraries

The power of the approach would be extended if the solution ligands comprised a mixture of molecules with different structures.

Again taking the example of oligonucleotides, we have found that different oligonucleotides open up different regions of tRNA$^{phe}$, and that each interaction permits its own set of interactions with other oligonucleotides. This analysis was done with each solution oligonucleotide separately. If it were possible to identify the bound solution oligonucleotide after the complex with the target were bound to the array, the solution ligands could comprise a mixture of all oligonucleotide sequences in a given size range. Ways to identify individual oligonucleotides or other analytes after they have been coupled to an array in this way are described in an earlier patent application GB 93 15 847.5 filed 30 July 1993.

The advantage of this double combinatorial approach could be very large; the number of interactions studied in a single analysis is equal to the product of the number of ligands on the array and in solution. For octanucleotides on the array and in solution, this would be $4^{16}$ '$4\times10^9$.

Linked ligands

Pairs or higher multiples of ligands act to increase binding to a folded molecule by inhibiting the competing reaction— reformation of the internal structure of the target molecule. They will also increase the rate of binding by opening the structure of the target. Both of these processes could be enhanced if the ligands were joined so that trimolecular or higher order interactions were reduced to bimolecular interactions. It is easy to imagine that a pair of oligonucleotides, including short ones such as di-, tri- and tetra-nucleotides, or other ligands, could be joined by a flexible linker that would allow them both to bind. The effect of linking the interacting moieties together could be further extended by enhancing the binding of one or more of the ligands to the target, for example, by covalent cross-linking, by chelation, by intercalation, or by charge or van der Waals interaction with the target molecule. This would allow other ligands more time to bind to the target. Linkers with other desirable qualities, such as greater cell permeability, could further improve the ligands' properties. A ligand could form the basis of a ribozyme, e.g. by having at least one portion for interacting with a target and another portion with catalytic activity.

EXAMPLES

Apparatus for making arrays

The device used to form the cell must make a good seal against the substrate on which synthesis takes place. We use glass for the substrate. Teflon is the only material we have found which makes a good seal to glass and withstands the solvents and chemicals used in oligonucleotide synthesis. The surface of the cell must be finished before machining the walls that create the reaction chamber, and we have been able to make a diamond shaped template that creates a good seal when pressed against a glass surface (Southern et al 1994). Alternatively, a circular template can be cut in a lathe in such a way that the surface tooling runs in the same lines as the cuts used when it is pressed against the glass surface (FIG. 2a). The depth of the cell is ca.0.5 mm. Inlet and outlet ports were made by drilling 1.0 mm diameter holes at the top and bottom of the circle and fitting sawn-off 19 gauge (1.1 mm o.d.) syringe needles through from the back. The Teflon cell was mounted on a rail fitted with a lead screw that was used to displace the glass plate relative to the Teflon reaction cell. A "G" clamp, fitted with a dished polyethylene cushion, was fixed to the rail to apply pressure to the glass plate and form the seal to the reaction cell. The rail was mounted on the front of the frame of an ABI 381A oligonucleotide synthesiser so that the delivery lines normally connected to the column could be connected to the reaction cell.

Making arrays

Glass plates (50×220×3 mm) were first coated with a covalently attached linker [Maskos and Southern, 1993]. Plates were immersed in a mixture of glycidoxypropyl trimethoxysilane/diisopropyethylamine/xylene (17.8:1:69, by volume), heated to 80° C. and held at this temperature for 9 h, and then washed in ethanol and ether. In a second step, the plates were heated in neat hexaethylene glycol, containing a catalytic amount of sulphuric acid, at 80° C. for 10 h, washed with ethanol and ether, air dried and stored at −20° C. Oligonucleotide synthesis used standard reagents for phosphoramidite chemistry, omitting the capping step. The ABI 381A was programmed to couple bases in the order corresponding to the complement of the target sequence, with an interrupt after deprotection. The scale was for 0.2 μmol. synthesis, adjusted slightly to provide volumes that would just fill the reaction chamber.

Final deprotection in 30% ammonia was carried out in a specially constructed bomb, comprising a chamber (230× 230×20 mm) cut into a Nylon block (300×300×30 mm), sealed by a sheet of silicone rubber (3 mm thick), compressed against the rim of the chamber by clamping the whole assembly between two mild steel plates (6 mm thick) using four bolts along each side of the square. After 5–8 h at 55° C. the bomb was cooled to 4° C. before opening. The plate was then washed in ethanol followed by Tris/EDTA (0.01M, pH 7.8, 0.1% SDS) and ethanol and then dried in an air stream.

Hybridisation reactions

We have used a variety of target molecules in experiments with scanning arrays: synthetic oligonucleotides labelled using polynucleotide kinase with gamma-$^{32}$P, gamma-$^{33}$P or gamma-$^{35}$S-ATP to tag the 5' end; RNAs labelled at the 3' end using RNA ligase with 5'-$^{32}$P cytosine-3',5'-diphosphate; or transcripts of DNA fragments made from PCR amplified fragments using T7 or SP6 polymerase to incorporate α-$^{32}$P or α-$^{35}$S UTP. All of these make good hybridisation targets. Most hybridisation reactions were carried out at 4–25° C., in solutions containing 3–4.5M TMACl or 1.0 M NaCl. After hybridisation, the plate was rinsed in the hybridisation solvent and exposed through Clingfilm to a storage phosphor screen (Fuji STIII) which was then scanned in a Molecular Dynamics 400A PhosphorImager.

In the specific examples shown in FIGS. 2 and 4, experimental conditions were as follows:

tRNA$^{phe}$ (10 pmol, Sigma) was dissolved in HEPES buffer (50 mM, pH7.4; 20 mM MgCl$_2$, 3.3 mM DTT, 1 μM ATP, 10 μg/ml BSA, 10% DMSO) with cytosine-3',5'-diphosphate (3000 Ci/mmol, Amersham), and T4 RNA ligase (9 units, Pharmacia), after 30 min incubation at 37°, the reaction was separated in a spun column and the labelled RNA dissolved in 3.5M TMA (10 ml). Hybridisation was carried out by applying ca. 1 ml of the solution to the surface of the array and overlaying a second glass plate of the same dimensions. The "sandwich" was placed in a sealed box at 4° C. for 18–24 h. The plates were separated, the array rinsed in the hybridisation solvent at 4° C., and analysed as described above.

For the cooperative experiments shown in FIG. 4, cold oligonucleotides corresponding to the D-loop GCTCTC-CCAACT (SEQ ID NO.1), the variable loop GACCTCCA-GATT (SEQ ID NO.2), or the TpsiC loop AACACAG-GACCT (SEQ ID NO.3), were incubated with the tRNA in the hybridisation conditions for at least 18 h before being applied to the plate.

Figures
FIG. 1.

Figure 3:
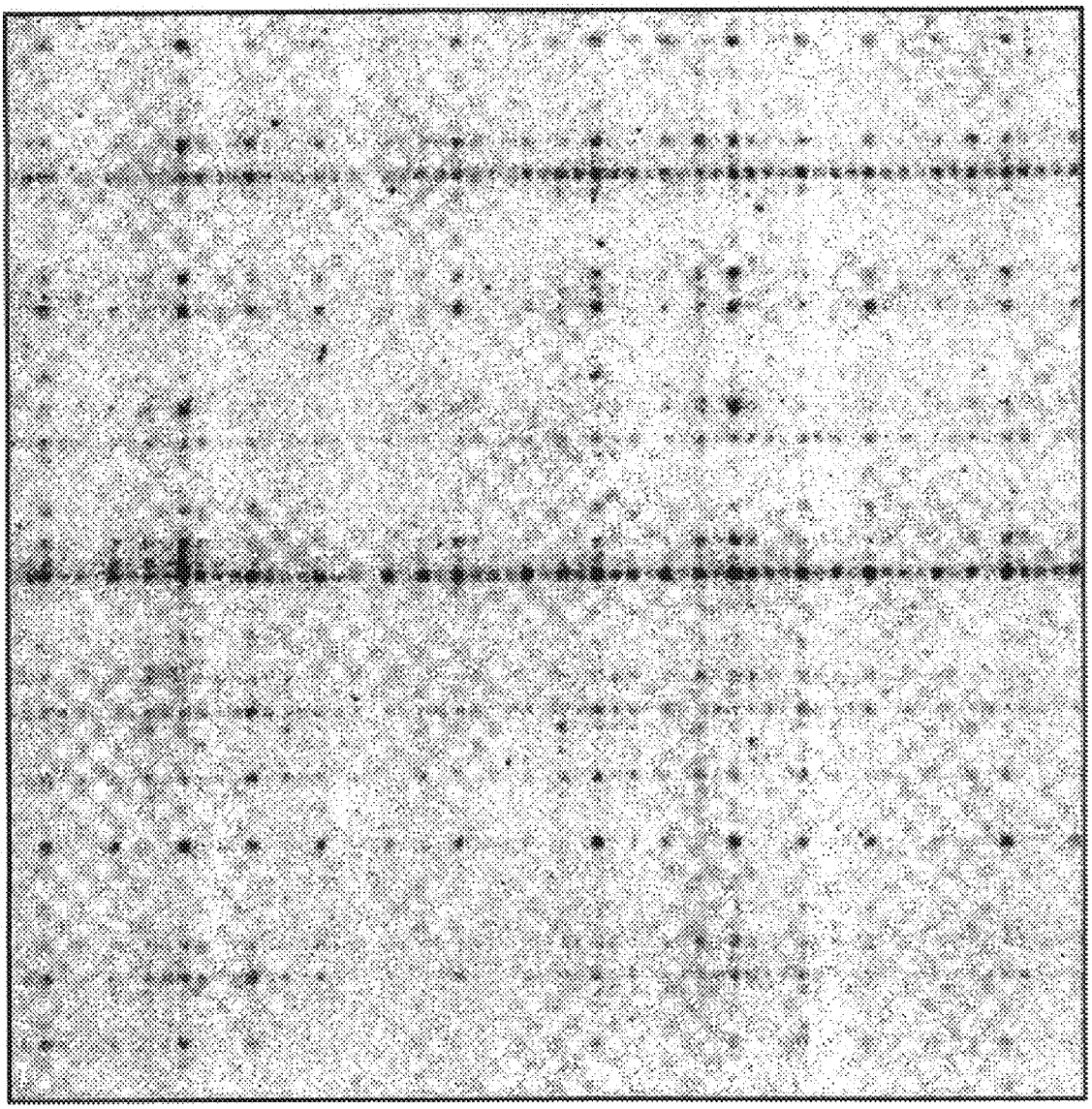
FIG. 3 shows hybridisation of tRNA$^{phe}$ to an array of type $N_3X_2N_3$.

An illustrative array comprising all tetranucleotide sequences. This is one sixteenth the size of the smallest usable array comprising all hexanucleotides, which would be too complex to display in this format. The letters along the top and down the left hand side show the order in which base precursors were applied in columns and rows during the synthesis of the oligonucleotides. The letters in each cell show the sequence of the oligonucleotide synthesised in that cell. Larger arrays are made by simply ovelaying increasingly wide rows and columns such that each successive row or column embraces four from the previous layer. In all cases, the array comprises all $4^s$ possible oligonucleotide sequences of length s. The results of hybridisation to such an array are shown in FIG. 3. More complex arrays can be made by applying mixtures of all four bases at certain stages in the synthesis; for example, all octanucleotides can be made in 4096 cells by applying four mixed bases in the two central positions, to produce an array of the type $N_3X_2N_3$. In this case, each cell comprises a mixture of 16 different octanucleotides. The results of hybridisation to such an array are shown in FIG. 3.

FIG. 2a.

Scanning arrays are made by applying oligonucleotide precursors to the glass substrate in a circular patch. The first base, corresponding to the complement of the 5' end base of the target sequence, is applied to the left end of the plate, which is then moved by a predetermined off-set, and the second base added. The process is repeated for the whole of the sequence. The length of oligonucleotides made on the centre line is equal to the diameter of the cell divided by the offset, in this case, diam.=30 mm and offset=2.5 mm, giving a maximum overlap of 30/2.5=12. Oligonucleotides ranging in size down to a single base are made in the segments flanking the centre line.

The upper panel shows a scanning array representing the 76 bases of tRNA$^{phe}$, hybridised to end labelled tRNA. Note the strong hybridisation in the region of the D-loop, more moderate hybridisation to the variable loop, and very weak hybridisation to the anticodon loop and the 5'-end of the molecule.

FIG. 2b.

The lower panel shows a scanning array representing 76 bases of HIV TAR element hybridised to an in vitro labelled transcript of the same region. Note the strong hybridisation to a single 12-mer, which is tenfold stronger than hybridisation elsewhere. This 12-mer corresponds to the region of the loop which has been shown by others [Ecker et al., 1992] to form a pseudo-half-knot with an adjacent 12-mer.

FIG. 3.

Hybridisation of a tRNA$^{phe}$ to an array of the type $N_3XXN_3$, where N is any one of the four bases and X is a mixture of all four, so that 65536 different octanucleotides are all present on the array, in cells containing mixtures of 16 related sequences. This result shows which regions of the sequence are most open to hybridisation. These can then be examined in detail on a scanning array, as shown in FIG. 2a.

FIG. 4.

Effects of including non-radioactive oligonucleotides (positions in the structure and the exact 12-mer indicated in the panel) with the tRNA target in the hybridisation solution. Note the large increase in binding to regions of the sequence that do not hybridise in the absence of the added oligonucleotides, showing that these regions have been opened up. The top panel is the control with no added oligonucleotide. The third and fourth panels show that adding a second oligonucleotide exposes regions that are not opened by the first oligonucleotide alone.

FIG. 5.

Cooperative antisense oligonucleotides against rabbit β-globin mRNA.

Much is known about the rabbit globin system. It was one of the first mRNAs to be isolated and characterised by translation in vitro. We have studied it because we wish to use it to study it as a model for antisense intervention. In preparation, we made a scanning array of oligonucleotides complementary to 122 bases around the initiation codon of the mRNA (atg marked in bold letters at bases 54–56). The folded structure shown in the figure is that with minimum free energy calculated by the energy minimisation program mfold, and displayed by squiggles. Hybridisation of labelled RNA showed interaction at the region complementary to bases 46–62 marked by a thick line on the molecule. We then made a deoxyribooligonucleotide corresponding to this 17-mer. Rehybridisation of the complex showed, as expected, no signal at the position of bases 46–62, but new signal at bases 32–45, marked with a dashed line. This is a surprising result, as there is no indication from the computer prediction that bases 46–62 interact with bases 32–45. On the contrary, there is a single stranded region of nine bases between them, which should be enough to decouple any interaction. Thus, the experiment suggests an interaction relevant to the design of antisense reagents which could not have been predicted by energy calculations or by examination of the computer generated structure.

FIG. 6.

Four arrays were made of complements to the same sequence, a region of the human CFTR gene (mutations in this gene are responsible for cystic fibrosis). The arrays were made as described in Southern et al (1994) on a glass substrate derivatised with a hexaethylene glycol linker.

a) natural deoxyribonucleotides tethered to the glass through the 3' ends.
b) natural deoxyribonucleotides tethered to the glass through the 5' ends.
c) deoxyribophosphothioates (Note that this array was exposed in the opposite orientation to the other three).
d) ribonucleotides.

The arrays were all hybridised under identical conditions (3.5 M tetramethylammonium chloride, 4° C.) with the sequence CCTGGCACCATTAAAGAAAATAT-CATCTTTGGTGTTTCCTAT (SEQ ID NO. 4), part of exon 10 of the CFTR gene covered by the array.

The deoxyribonucleotides give essentially the same result in both chemical orientations, but the analogues, the deoxyribophosphothioates and ribonucleotides, give quite different results. Although a difference may be expected, this experiments shows the difficulty in extrapolating data from one analogue to others, and further demonstrates the power of the array technique in identifying candidates for antisense reagents, including analogues.

Figure 7A:
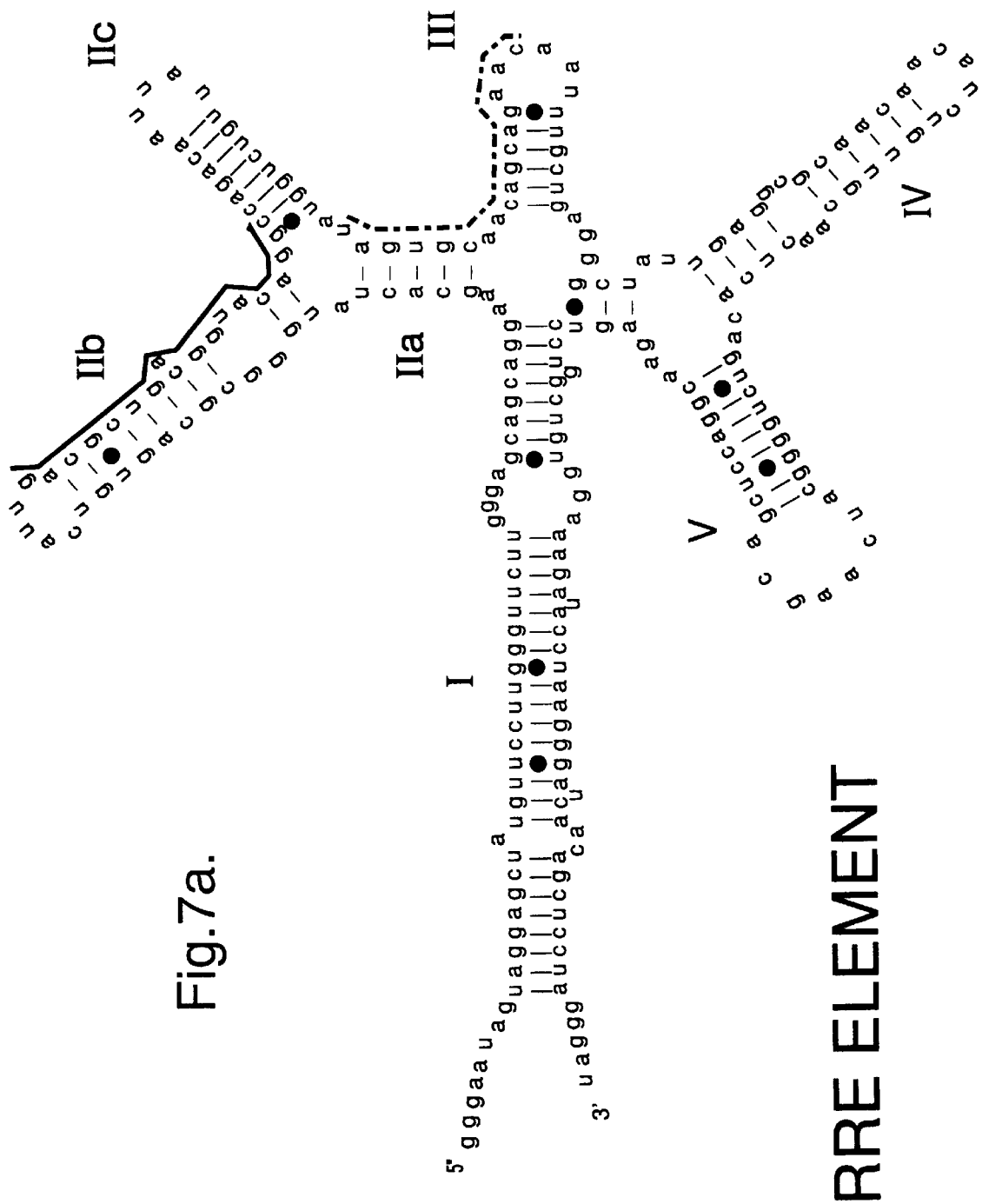
FIG. 7(a) shows a folded structure of the Rev response element (RRE) of HIV RNA derived from computer molecular modelling.
Figure 7B:
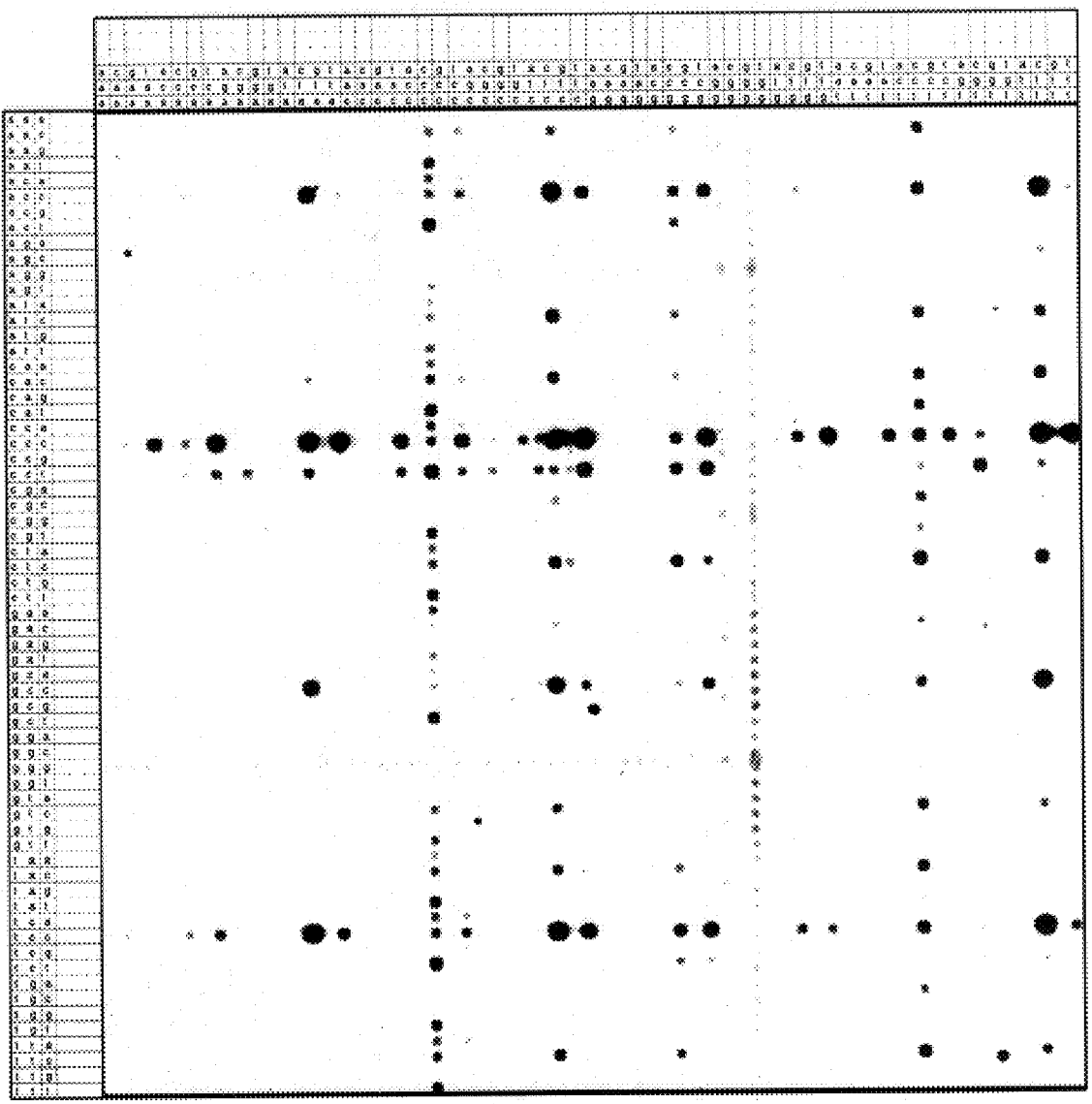
FIGS. 7(b) and (c) show the hybridisation of labelled RRE HIV RNA to two universal arrays.
Figure 7C:
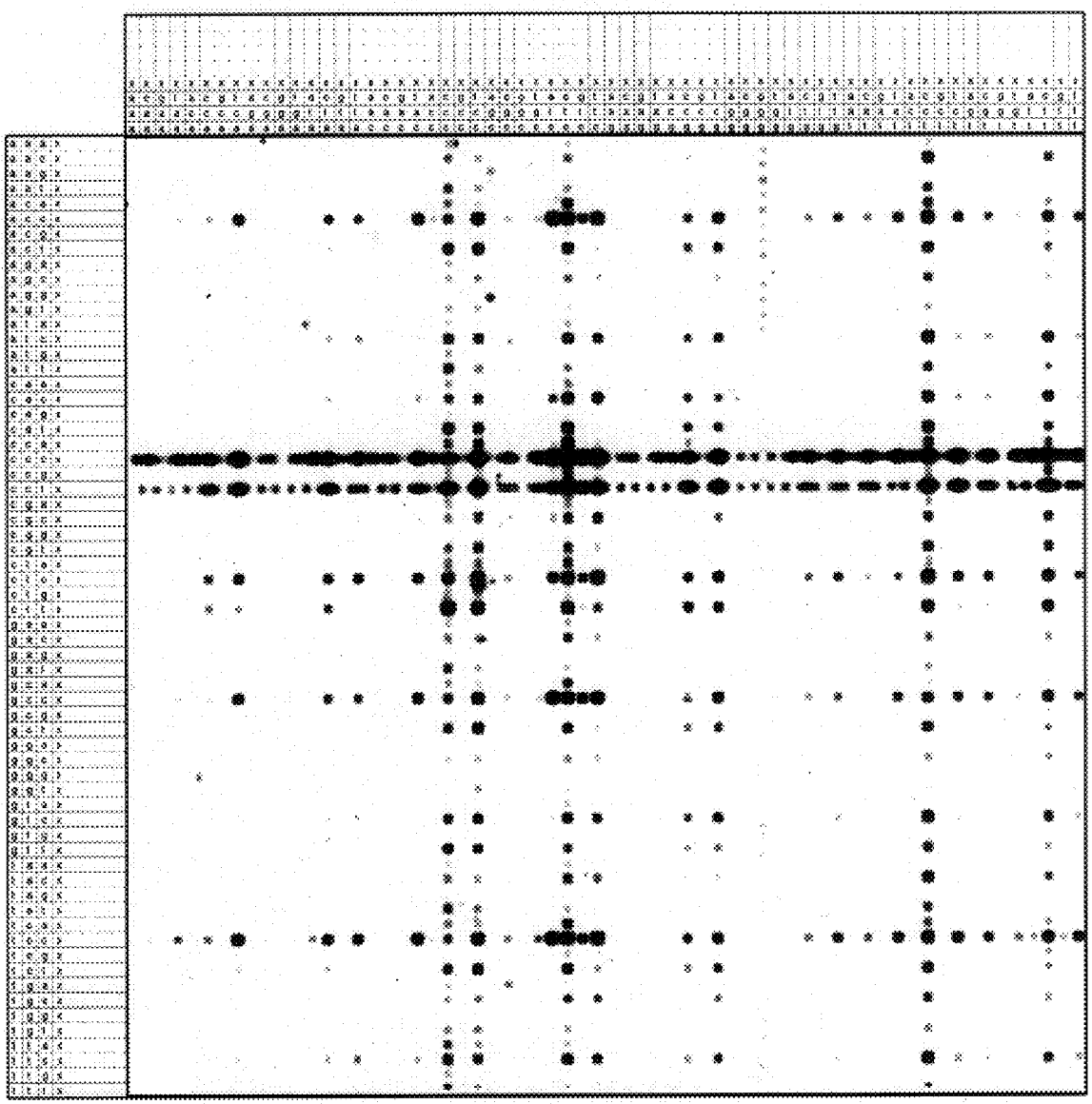

FIGS. 7(a)–7(c)

The Rev response element (RRE) of HIV is considered to be a good potential target for therapeutic intervention by antisense oligonucleotides because of its central place in the regulation of gene expression from the viral genome. However, molecular modelling in the computer, as shown (FIG. 7a), suggests that this region of HIV RNA is likely to have a complex folded structure, and this has been confirmed by analysing the susceptibility of the RNA to nucleases. This structure makes it difficult to select regions for antisense targetting. We have analysed the hybridisation behaviour in a two stage process. First, the labelled RNA was hybridised to "universal" arrays, that is arrays comprising all oligonucleotides of a chosen length. In this experiment, we used two types of universal arrays, one comprising all 4096 hexanucleotides (FIG. 7b), the other all 65,536 octanucleotides (FIG. 7c). In the latter array there were only 4096 cells, each containing a mixture of sixteen different octanucleotides of the general form NNNXXNNN, where N is a defined base, and X is a mixture of all four. These universal arrays do not indicate the optimum oligonucleotide to use, as they only have sequences of limited length, but they do reveal the regions in the target sequence which are most available for hybrid formation. These areas were then analysed in more detail using scanning arrays as described below. The method used to make the universal arrays produces oligonucleotides half the length of the major oligonucleotides in lines which intersperse them. A surprising result of the analysis is that some of these tri- and tetranucleotides interact strongly with the target (see the lines of uniform intensity in FIGS. 7a and b). With other targets we see the same feature, but with different oligonucleotide sequences. In one case (Southern et al, 1994), we have seen interaction between a target and a dinucleotide. It is likely that these interactions are the result of the folding of the target RNA, which may present short stretches of sequence in a structure which is particularly favourable for interaction with oligonucleotides; for example, a stacked half helix. These observations suggest a novel approach to antisense design, based on the use of array analysis. Namely, that short oligonucleotides, which are seen to interact in this structure specific manner can be incorporated in the cocktail of antisense agents specific to the target, either as a component of a mixture, or as a component of a linked composite molecule.

Figure 8A:
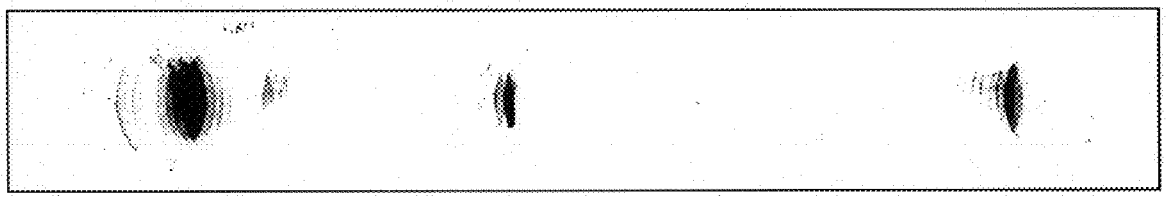
FIGS. 8(a), (b) and (c) show scanning arrays of the region of RRE analyzed in FIG. 7.
Figure 8B:
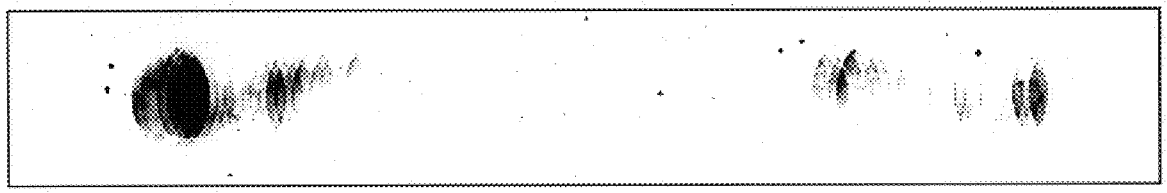
Figure 8C:
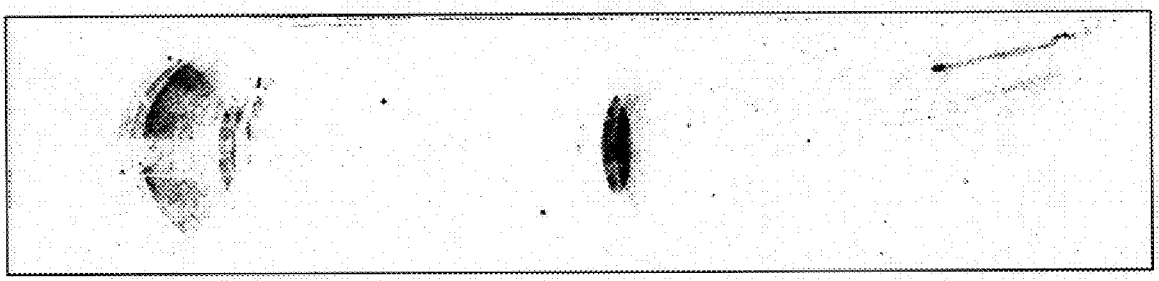

FIGS. 8(a)–8(c)

The region of the RRE analysed in FIG. 7 was also analysed on a scanning array made of oligodeoxyribooligonucleotides with 17 mers as the longest. Only one oligonucleotide in the Rev binding region showed strong interaction at 37° C. in 3.5 M TMACl (FIG. 8a). When this oligonucleotide was bound to the target in solution and the complex again applied to the array, several sites showed interaction with oligonucleotides which had not bound in the absence of the solution oligonucleotide (FIG. 8b). The same region bound when the RRE target was analysed on an array of phosphothioate analogue oligonucleotides at 20° C. in 1 M NaCl (FIG. 8c).

Figure 9A:
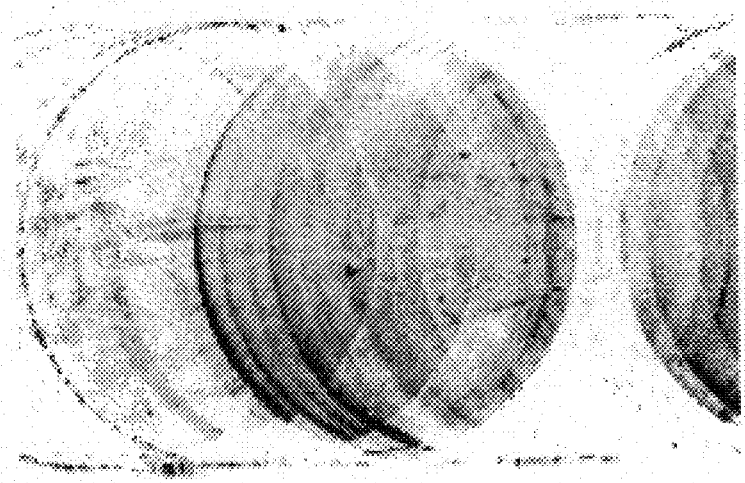
FIGS. 9(a) and (b) show the analysis described in FIG. 8 conducted to presence of neomycin.
Figure 9B:
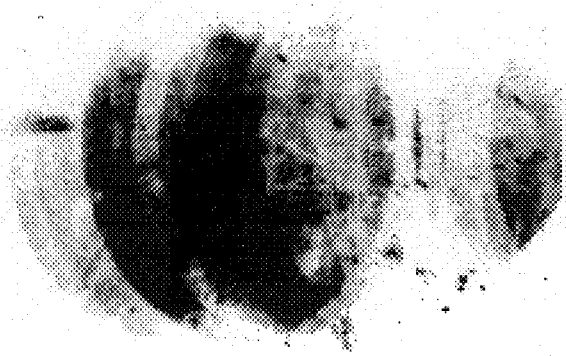

FIGS. 9(a)–9(b)

The analysis described in FIG. 8 was repeated in the presence of neomycin, a drug which is known to act by binding to RNA molecules. The presence of neomycin substantially altered the pattern of interaction of RRE with some oligonucleotides. (FIGS. 9a and b). In particular, regions which bind poorly in its absence bind more strongly in its presence.

Figure 10A:
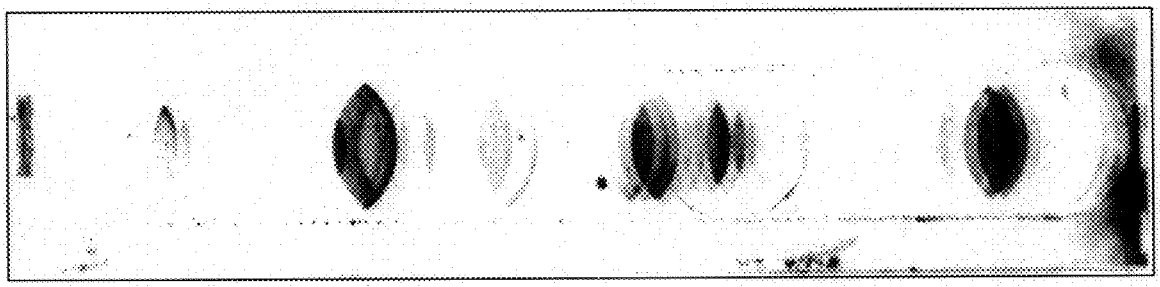
FIGS. 10(a) and (b) show the effect of magnesium ions on the folding behavior of RNAs.
Figure 10B:

FIGS. 10(a)–10(b)

Magnesium is known to have a significant effect on the folding behaviour of RNAs and we have examined its effect on the binding behaviour of tRNA using the scanning array used in the experiments described in FIGS. 2a and 4. We find that several oligonucleotides which do not bind in the absence of magnesium ions (FIG. 10a) do so in its presence (FIG. 10b).

FIGS. 11(a)–11(b)

Figure 11C:
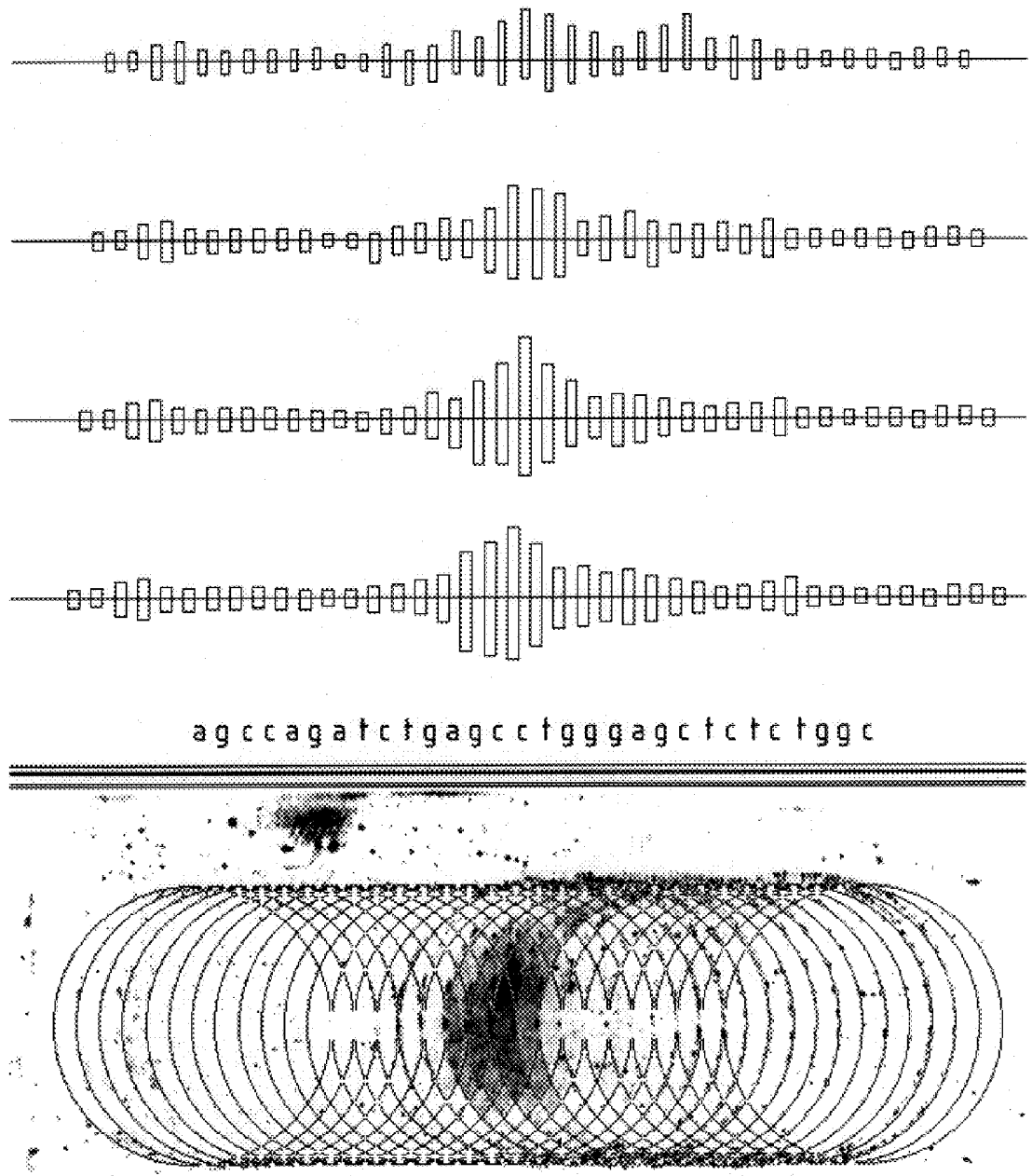
FIGS. 11(a), (b) and (c) show the analysis of the TAR element of HIV using the method of this invention.

The TAR element is another important target for HIV. We have analysed its hybridisation behaviour with arrays of natural oligodeoxyribonucleotides, and with an array made with analogues that are commonly used as antisense agents, 2'-O-methylribonucleotides (FIG. 11c). The same region is found to hybridise in both cases, the loop of the stem-loop, but only one or two sequences in this region form duplex, and the exact position of the sequence with strongest interaction is different with each analogue. In an experiment with the natural oligodeoxyribonucleotides, we selected an antisense sequence as the "pioneer" (FIGS. 2b and 11a) and used it to open the structure. Note the loss of binding in the region corresponding to the solution ligand, and the additional binding at other sites. When the complex was bound to the array, several oligonucleotides which had not bound in its absence, now gave a significant yield of duplex (FIG. 11b).

Conclusion

The above examples illustrate several new approaches to the design, characterisation and discovery of ligands made possible by analysis on arrays on solid supports. We have shown how this approach can:

Identify regions of the target that are open to interaction with ligands;

Identify combinations of ligands that act together to give a different, usually stronger, interaction than either alone;

Discover regions of the target that are structured in such a way as to allow them to bind in unexpected ways, e.g. target RNAs to very short oligonucleotides;

The arrays and the cooperative ligands used in the examples were made of a variety of chemical types, illustrating the generality of the approach.

REFERENCES

1. James, W. (1991). Towards gene-inhibition therapy: a review of progress and prospects in the field of antiviral antisense nucleic acids and ribozymes. Antiviral Chemistry and Chemotherapy 2(4): 191–214.
2. Maskos, U. and Southern, E. M. (1992a). Parallel analysis of oligodeoxyribonucleotide interactions. I. Analysis of factors influencing oligonucleotide duplex formation. Nucleic Acids Research 20: 1675–1678.
3. Maskos, U and Southern, E. M. (1992b). Oligonucleotide hybridisations on glass supports: a novel linker for oligonucleotide synthesis and hybridisation properties of oligonucleotides synthesised in situ. Nucleic Acids Research 20: 1679–1685.
4. Maskos, U. and Southern, E. M. (1993a). A novel method for the analysis of multiple sequence variants by hybridisation to oligonucleotides. Nucleic Acids Research 21: 2267–2268.
5. Maskos, U. and Southern, E. M. (1993b). A novel method for the parallel analysis of multiple mutations in multiple samples. Nucleic Acids Research 21: 2269–2270.
6. Morgan, R., Edge, M., and Coleman, A., (1993). A more efficient and specific strategy in the ablation of mRNA in *Xenopus laevis* using mixtures of antisense oligos. Nucleic Acids Research 21: 4615–4620.
7. Offensperger, W- B., Offensperger, S., Walter, E., Teubner, K., Igloi, G., Blum, H. E. and Gerok, W. (1993). In vivo inhibition of duck hepatitis B virus replication and gene expression by phosphorothioate modified antisense oligodeoxynucleotides. EMBO J. 12: 1257–1262.
8. Southern, E. M., Maskos, U. and Elder, J. K. (1992). Analysis of Nucleic Acid Sequences by Hybridization to Arrays of Oligonucleotides: Evaluation using Experimental Models. Genomics 12: 1008–1017.

9. Southern, E. M., Case-Green, S. C., Elder, J. K., Johnson, M., Mir, K. U., Wang, L. and Williams, J. C. Arrays of complementary oligonucleotides for analysing the hybridisation behaviour of nucleic acids. Nucleic Acids Research 1994, Vol. 22, No. 8, 1368–1373.
10. Matson, R. S., Rampal, J. B. and Coassin, P. J., Biopolymer synthesis on polypropylene supports I oligonucleotides, Analyt. Bioch. 217, 306–310 (1994).

What is claimed is:

1. A method of investigating the intramolecular structure of a polynucleotide, which method comprises:

providing a polynucleotide, said polynucleotide having a known sequence and having an intramolecular structure, and providing a plurality of different oligonucleotides in the form of an array on a solid surface,

---

SEQUENCE LISTING (1) GENERAL INFORMATION:

(iii) NUMBER OF SEQUENCES:  4

(2) INFORMATION FOR SEQ ID NO:1:

(i) SEQUENCE CHARACTERISTICS:
      (A) LENGTH:  12 bases
      (B) TYPE:  nucleic acid
      (C) STRANDEDNESS:  single
      (D) TOPOLOGY:  linear (ii) MOLECULE TYPE: other nucleic acid, synthetic DNA (xi) SEQUENCE DESCRIPTION: SEQ ID NO:1:

GCTCTCCCAA CT                                          12

(2) INFORMATION FOR SEQ ID NO:2:

(i) SEQUENCE CHARACTERISTICS:
      (A) LENGTH:  12 bases
      (B) TYPE:  nucleic acid
      (C) STRANDEDNESS:  single
      (D) TOPOLOGY:  linear (ii) MOLECULE TYPE:  other nucleic acid, synthetic DNA (xi) SEQUENCE DESCRIPTION: SEQ ID NO:2:

GACCTCCAGA TT                                          12

(2) INFORMATION FOR SEQ ID NO:3:

(i) SEQUENCE CHARACTERISTICS:
      (A) LENGTH:  12 bases
      (B) TYPE:  nucleic acid
      (C) STRANDEDNESS:  single
      (D) TOPOLOGY:  linear (ii) MOLECULE TYPE:  other nucleic acid, synthetic DNA (xi) SEQUENCE DESCRIPTION: SEQ ID NO:3:

AACACAGGAC CT                                          12

(2) INFORMATION FOR SEQ ID NO:4:

(i) SEQUENCE CHARACTERISTICS:
      (A) LENGTH:  42 bases
      (B) TYPE:  nucleic acid
      (C) STRANDEDNESS:  single
      (D) TOPOLOGY:  linear (ii) MOLECULE TYPE:  other nucleic acid, synthetic DNA (xi) SEQUENCE DESCRIPTION: SEQ ID NO:4:

CCTGGCACCA TTAAAGAAAA TATCATCTTT GGTGTTTCCT AT                42 all of said different oligonucleotides being fully complementary to different segments of the polynucleotide;

applying the polynucleotide in solution to the array of oligonucleotides under hybridisation conditions which preserve the intramolecular structure of the polynucleotide; and observing quantitative differences between interactions of the polynucleotide with different oligonucleotides of the array, said differences between interactions being indicative of the intramolecular structure of the polynucleotide.

2. The method according to claim 1, wherein the polynucleotide is an RNA.

3. The method according to claim 1, wherein the polynucleotide is a DNA.

4. The method according to claim 1, which further comprises an additional step of designing an antisense oligonucleotide based upon said quantitative differences.

5. A method of identifying oligonucleotides which specifically bind to a polynucleotide, which method comprises:

a) binding at least one oligonucleotide to the polynucleotide to form a polynucleotide-oligonucleotide complex, b) applying the polynucleotide-oligonucleotide complex to an array comprising a plurality of different oligonucleotides immobilized on a solid surface under hybridisation conditions which allow for interaction between the array of immobilized oligonucleotides and the polynucleotide-oligonucleotide complex, and c) identifying an immobilized oligonucleotide on the array which specifically binds to the polynucleotide-oligonucleotide complex.

6. The method as claimed in claim 5, wherein one oligonucleotide is bound to the polynucleotide in step a) to form the polynucleotide-oligonucleotide complex, and then steps b) and c) are conducted.

7. The method as claimed in claim 5, wherein two or more oligonucleotides are bound to the polynucleotide in step a) to form the polynucleotide-oligonucleotide complex, and then steps b) and c) are conducted.

8. The method as claimed in claim 5, wherein the at least one oligonucleotide to be bound to the polynucleotide to form the polynucleotide-oligonucleotide complex in step a) is chosen by mixing the polynucleotide with a library of oligonucleotides and choosing from the library at least one oligonucleotide that binds to the polynucleotide.

9. The method as claimed in claim 5, wherein the polynucleotide is an RNA.

10. The method as claimed in claim 5, wherein the polynucleotide is a DNA.

11. The method as claimed in claim 5, wherein the polynucleotide has a secondary or tertiary structure, and wherein the polynucleotide-oligonucleotide complex is caused to interact with the array of oligonucleotides under hybridisation conditions, whereby the secondary or tertiary structure of the polynucleotide is retained during hybridisation.

12. The method as claimed in claim 5, wherein the polynucleotide has a known sequence.

13. The method as claimed in claim 5, which further includes a step of designing an antisense oligonucleotide based upon the identification of the immobilized oligonucleotide.

* * * * *